United States Patent [19]

Swanson et al.

[11] Patent Number: 5,179,706
[45] Date of Patent: Jan. 12, 1993

[54] METHOD AND APPARATUS FOR PREVENTING BUS CONTENTION PROBLEMS BETWEEN TWO PROCESSORS

[75] Inventors: Scott C. Swanson, Roswell; Jeffrey P. Murray, Decatur, both of Ga.

[73] Assignee: Hayes Microcomputer Products, Inc., Norcross, Ga.

[21] Appl. No.: 428,858

[22] Filed: Oct. 30, 1989

[51] Int. Cl.$^5$ ............................................... G06F 3/04
[52] U.S. Cl. ................................... 395/725; 364/270.6; 364/270.9; 364/271.7; 364/DIG. 1; 364/950.2; 364/DIG. 2
[58] Field of Search .................... 364/200, DIG. 1; 395/325, 725

[56] References Cited

U.S. PATENT DOCUMENTS 4,543,629 9/1985 Carey ..................................... 364/200

Primary Examiner—Michael R. Fleming
Assistant Examiner—Clifford Knoll
Attorney, Agent, or Firm—Jones, Askew & Lunsford

[57] ABSTRACT

A bus access controller. An interface circuit (22) controls the access of a host computer (10) and a microprocessor (23) to one or more UARTs (14, 15). The microprocessor (23), which has no provision for waiting for a data transfer, is required to provide a signal of its intent to perform a data transfer prior to beginning the actual data transfer. The signal is identical to the actual data transfer operation. If the host (10) attempts a data transfer operation while the microprocessor (23) is conducting a data transfer operation, or if the host data transfer cannot be completed prior to the time that the microprocessor data transfer will commence, then the interface circuit (22) signals the host (10) that the data transfer will take additional time by deasserting the I/O READY line (12a). Once the microprocessor data transfer is completed then the I/O READY signal is reasserted and the host data transfer is completed. Bus contention problems and data loss are therefore prevented and the host (10) waiting time is minimized.

22 Claims, 2 Drawing Sheets

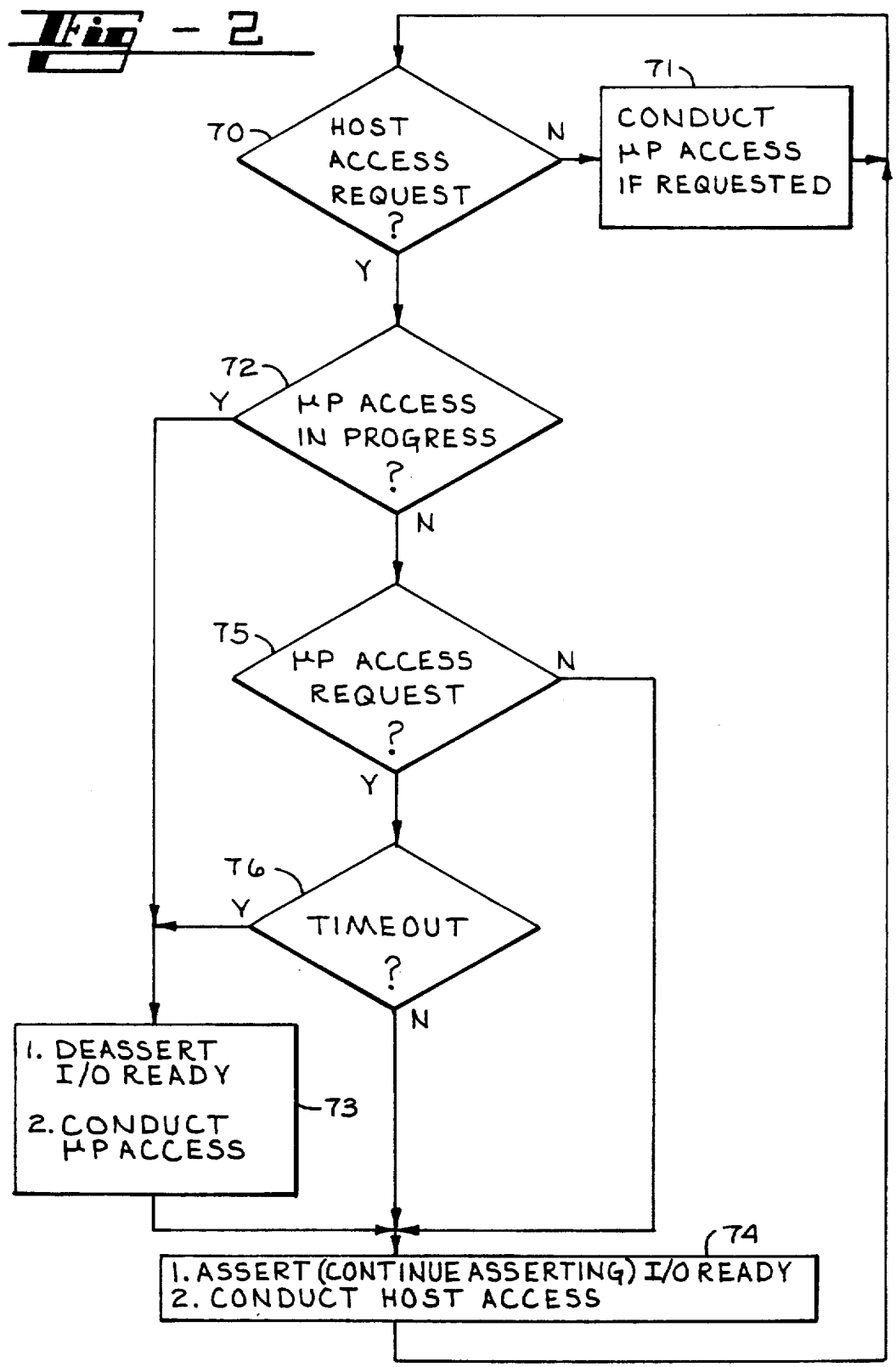

METHOD AND APPARATUS FOR PREVENTING BUS CONTENTION PROBLEMS BETWEEN TWO PROCESSORS

TECHNICAL FIELD

The present invention relates to data processing systems and, more particularly, describes a method and apparatus for preventing bus contention problems between two processors by controlling access to a common bus.

BACKGROUND OF THE INVENTION

There are numerous software programs and hardware devices currently available which allow asynchronous serial communications to be performed by a host computer. The hardware devices typically contain a universal asynchronous receiver transmitter (UART), such as the 8250, 16450, or 16550, manufactured by National Semiconductor, Santa Clara, Calif. The software programs are designed to support one or more of these UART types. A typical serial communications card, which contains a UART, will function without difficulty up to and exceeding 19,200 bits per second (bps). However, in the case of the 8250 and the 16450 UARTs, each time a complete byte is received an interrupt must be generated and the host must read the received byte prior to completion of receipt of the next byte by the UART. Otherwise, data will be lost. Therefore, each time a complete byte is received the host computer must stop its current operation and execute an interrupt service routine which services the UART by reading the received byte. At low serial data rates this procedure does not present a problem. However, at higher data rates, the amount of time required to execute the service routine and retrieve the received byte may occupy substantially all of the host computer's processing time, thus leaving little or no time for the performance of other operations. The use of a 16550 UART, which has a 16 byte buffer, eliminates the need for immediate attention to an interrupt from the UART. However, the host computer must still service the UART at a sufficient rate to prevent the buffer from filling up or data will be lost.

The host computer may, of course, send through the UART a flow control command to a remote device which causes the remote device to stop sending data. However, the host computer must execute a flow control routine and several additional characters may be received before the remote device stops sending data.

Therefore, it is desirable to have a serial data communications device which provides enhanced functions such as additional buffering, automatic flow control, and direct memory access (DMA) data transfer. Of course, to use the enhanced functions the host computer must use a software program which was written to make use of the enhanced functions. The enhanced functions are most conveniently provided by the use of a microprocessor on the serial communications card. However, it is also desirable that the serial communications card be capable of providing enhanced functions and be compatible with software programs which do not support the use of the enhanced functions. Therefore, it is necessary that both the host computer and the microprocessor be able to access, when appropriate, the UART on the serial communications card. Because both the host computer and the microprocessor have access to the UART a data loss will occur if the host computer attempts to access the UART at the same time that the microprocessor was attempting to access the UART.

Furthermore, in a serial communications card which has two or more UARTs, each of which is independently configurable to achieve a desired serial interface, a data loss could occur if the host computer attempts to access one of the UARTs at a time when the microprocessor is attempting to access another of the UARTs. The bus contention problem between the host computer and the microprocessor becomes even more severe as serial data rates increase and both devices must access the bus more frequently in order to communicate with their respective UARTs.

Therefore, there is a need for a method and for an apparatus which prevents bus contention problems between two devices.

There is also a need for a bus management method and a bus management apparatus which prevent a loss of data when both the host computer and the microprocessor attempt to access the bus at the same time.

There is also a need for a method and for an apparatus for determining which of two devices will be able to access a bus at a particular time.

There is also a need for a method and for an apparatus which will deny a device access to a bus and advise the device that a requested data transfer will require additional time to execute.

SUMMARY OF THE INVENTION

The present invention provides a method and an apparatus whereby a host computer and a microprocessor can both access a third device, such as a UART, without bus contention problems. Furthermore, the host computer and the microprocessor transfer data with the UART without taking any steps to determine whether the other device is transferring data with the UART.

A typical host computer is a fast device which has the capability to communicate with a slow input/output (I/O) device. For example, the host computer may have an I/O READY input which can be used to advise the host computer whether a requested I/O transfer is complete. The slow device deasserts I/O READY until the data transfer has been completed. The slow device then asserts the I/O READY signal to advise the host computer that the data transfer is complete. The host computer waits until the I/O READY signal is asserted before proceeding to the next step. A typical microprocessor has no ability to communicate with a slow I/O device. More particularly, the microprocessor does not have a I/O READY signal input. Therefore, the microprocessor always completes the data transfer during the execution time for the instruction being performed.

In the present invention an interface circuit controls the access of the host computer and the microprocessor to the UART. The microprocessor signals the interface circuit that the microprocessor is going to access the UART on the next microprocessor instruction cycle. In the present invention the microprocessor accomplishes a data transfer by performing the transfer two times. That is, the microprocessor sends two read signals or two write signals, as appropriate. The first signal indicates that the microprocessor intends to perform a data transfer while the second signal is the actual data transfer. This method is advantageous in that a special command or special signal is not required to be generated or dedicated for the purpose of notifying the interface circuit that a data transfer is about to occur.

Once the first read or write signal occurs the interface starts a timer. The host computer is a fast device and can accomplish a data transfer during the period between the time the microprocessor sends the first signal and the time the microprocessor sends the second signal to begin the actual read or write operation. Therefore, the interface circuit will allow the host computer to perform a data transfer, even after the microprocessor has sent the first signal, provided that the host computer data transfer can be completed before the microprocessor data transfer is started. Any request for a data transfer attempted by the host computer before a predetermined cutoff time following the first signal by the microprocessor is allowed to be executed. Any host computer request for data transfer after this predetermined time will be delayed with the I/O READY signal until the microprocessor has completed its data transfer. Once the microprocessor has completed its data transfer then the data transfer requested by the host computer is completed and then the I/O READY signal is reasserted so that the host computer can move on to its next step.

During the period that the data transfer by the microprocessor is occurring a bidirectional, three state buffer is used to isolate the host computer from the UART, interface circuit, and microprocessor.

Therefore, it is an object of the present invention to allow a fast device and a slow device to access a peripheral device over a common bus and without bus contention problems.

It is another object of the present invention to use a signal to delay the operation of a fast device so that a slower device may perform a data transfer.

It is another object of the present invention to minimize an access delay for a data transfer by a host computer by accomplishing the data transfer in the period between instruction execution of a microprocessor.

It is another object of the present invention to provide an indication that a device intends to perform a data transfer by having that device perform a dummy data transfer prior to the actual data transfer.

BRIEF DESCRIPTION OF THE DRAWING

FIG. 2 is a flow chart of the operation of the interface circuit of the present invention.

DETAILED DESCRIPTION

Figure 1:
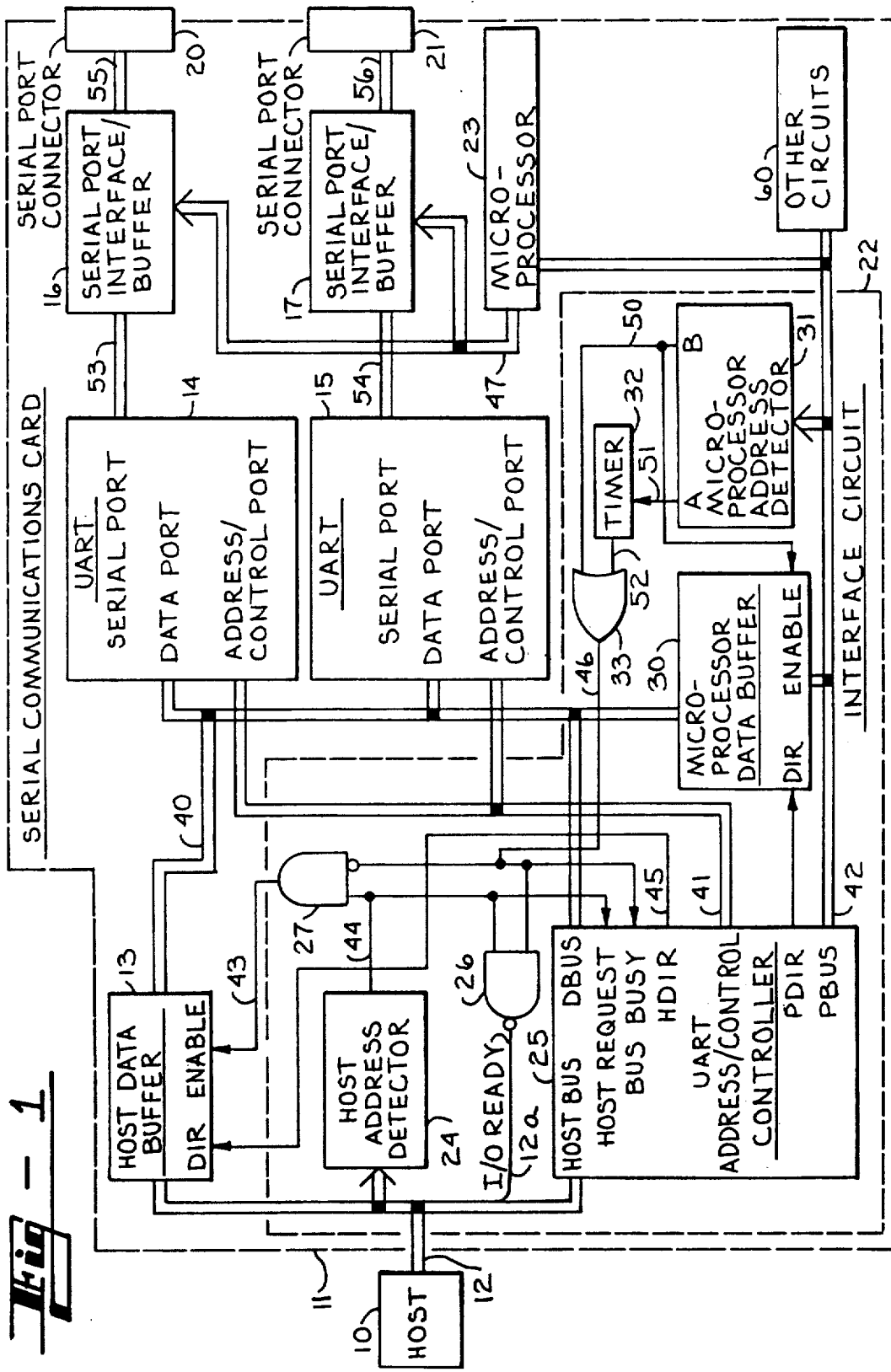
FIG. 1 is a schematic diagram of the preferred embodiment of the present invention in its preferred environment.

Turn now to the drawing, in which like numerals represent like components throughout the several figures. FIG. 1 is a schematic diagram of the preferred embodiment of the present invention in its preferred environment. Host computer 10 is connected to a dual channel asynchronous serial communications card 11 via host bus 12, which represents the host 12 address, data and control buses. Card 11 is installed in an expansion slot in host 10. Card 11 contains a host data buffer 13, two National Semiconductor NS16550 universal asynchronous receiver transmitters (UARTs) 14 and 15, which are herein considered to be peripheral devices, two serial port interface/buffers 16 and 17, two serial port connectors 20 and 21, an interface circuit 22, and an Intel 8031 microprocessor 23. In the preferred embodiment, interface circuit 22 is implemented by a gate array. However, interface circuit 22 may, if desired, be implemented by a microprocessor. The construction and operation of interface circuit 22 will be apparent to one of ordinary skill in the art after a reading of the functions performed by interface circuit 22, described below. In the preferred environment host 10 is an IBM PS/2, XT, AT or PC, or other compatible computing machine. In the preferred environment serial port connectors 20 and 21 are each connected to a communication device (not shown), such as a modem. Serial port connectors 20 and 21 preferably define an EIA RS-232-D serial interface. UARTs 14 and 15 convert data between a serial data format on connectors 20 and 21 and a parallel data format on bus 40. UARTs 14 and 15 are connected to serial port interface/buffers 16 and 17, respectively, by buses 53 and 54, respectively. Buffers 16 and 17 are connected by buses 55 and 56, respectively, to serial port connectors 20 and 21, respectively. Buffers 16 and 17 perform standard buffering functions between UARTs 14 and 15, respectively, on one side and connectors 20 and 21, respectively, on another side. Microprocessor 23 is connected to interface/buffers 16 and 17 via control bus 47. Interface/buffers 16 and 17, in conjunction with UARTs 14 and 15 and microprocessor 23, also perform standard flow control functions as well as enhanced and automatic flow control functions. The flow control functions performed by interface/buffers 16 and 17 use the standard data terminal ready (DTR) and ready to send (RTS) signals of EIA RS-232-D.

Card 11 is designed to be compatible with existing software drivers which expect to find a single UART at a predetermined address. However, in the preferred environment host 10 contains driver software designed to use both UARTs on card 11 as well as the additional features provided by card 11. Some of these additional features are first in, first out (FIFO) buffers for both transmit and receive modes, automatic flow control for data incoming on serial port connectors 20 and 21, and direct memory access (DMA) data transfer of data between a memory in host 10 and the FIFOs in card 11. For additional details the reader is referred to co-pending U.S. patent application Ser. Nos. 07/428,870, 07/429,065, and 07/429,150 now abandoned, filed concurrently herewith, all of which are hereby incorporated herein by reference.

Host 10 may use only UART 14 or UART 15, or may be using both UARTs simultaneously. Furthermore, one UART, such as UART 14, may be configured as a standard UART, such as the 8250 or the 16450, while the other UART, such as UART 15, may be independently configured to work with microprocessor 23 so that data transfers are by direct memory access. It will be noted that UARTs 14 and 15 share a common data bus 40 which connects them to host data buffer 13, controller 25, and microprocessor data buffer 30. Buffers 13 and 30 are bidirectional, three state buffers. UARTs 14 and 15 also share a common address/control bus 41, which connects them to controller 25. Host data buffer 13 and controller 25 are connected by host bus 12 to host 10. Similarly, controller 25 and microprocessor data buffer 30 are connected by processor bus 42 to microprocessor 23 and other circuits 60, such as memory devices and address latches. Because of the common buses 40 and 41 host 10 and microprocessor 23 must be restrained in their ability to place data, address and control signals on these buses or there will be a bus contention problem with subsequent loss of data. In the preferred embodiment, interface circuit 22 controls the access of host 10 and microprocessor 23 to buses 40 and 41 and therefore to UARTs 14 and 15. In order for interface circuit 22 to achieve this control microprocessor 23 is programmed to give a first signal which indicates that microprocessor 23 intends to access a UART for a data transfer operation, such as a read operation or a write operation. The data to be transferred may be data sent or received over serial connectors 20 or 21 or may be control data for or status data from UARTs 14 and/or 15. In the preferred embodiment, the first signal is the same as the signal required for the actual read or write operation that is intended. Therefore, microprocessor 23 simply sends the read or write signal twice. This method was chosen because it imposes less overhead on the microprocessor. Another signal from microprocessor 23 could be used but care must be taken that the signal is not used for operations other than data transfer operations with UARTs 14 and 15. Also, using the same signal for both the first signal and the data transfer reduces the possibility of an error.

Microprocessor address detector 31 monitors the addresses placed on processor bus 42 by microprocessor 23. A valid address detection occurs whenever an address occurs on bus 42 which indicates that a data transfer is intended for UART 14 or UART 15. On the occurrence of the first signal microprocessor address detector 31 will, via the A output and signal path 51, activate timer 32. The output of timer 32 is connected by signal path 52 to one input of an OR gate 33. The output of gate 33 is connected by signal path 46 to the BUS BUSY input of controller 25, one input of a two-input NAND gate 26, and to the negated input of a two-input AND gate 27. The output of gate 26 is the I/O READY signal on conductor 12a of host bus 12. The output of gate 27 is connected by conductor 43 to the ENABLE input of buffer 13. The B output of address detector 31 is connected by signal path 50 to the ENABLE input of data buffer 30 and to the other input of OR gate 33. A host address detector 24 monitors the address signals on host bus 12 and, if the address indicates that a data transfer is intended for UARTs 14 or 15 then address detector 24 will provide a logic 1, via signal path 44, to the input of gates 26 and 27 and to the host request input of controller 25.

Assume first that microprocessor 23 is not attempting to access UARTs 14 or 15 and that host 10 attempts a data transfer with one of the UARTs, for example, UART 14. Host address detector 24 will detect the UART 14 address on bus 12 and place a logic 1 on conductor 44. The A and B outputs of detector 31 will be logic 0, so the output of gate 33 will be a logic 0, and the output of gate 26 will be forced to a logic 1 state, indicating that the I/O operation may proceed. The logic 0 on conductor 46, along with the logic 1 on conductor 44, causes the output of gate 27 to be a logic 1, thereby enabling buffer 13. Therefore, host 10 is connected to UART 14 via buffer 13 and bus 40. Controller 25 monitors the host bus to determine whether a read or a write operation is occurring and sends the appropriate signals to UART 14 over bus 41 and also sends the appropriate signal to the direction (DIR) input of buffer 13 over conductor 45. The DIR input of buffer 13 controls the direction in which data is allowed to flow. A logic 1 on the ENABLE input of buffer 13 enables the buffer whereas a logic 0 forces the buffer into an open circuit output condition, thereby isolating host 10 from bus 40.

For the second case, assume that microprocessor 23 has sent the first data transfer signal but timer 32 has not reached a predetermined value and processor 23 has not sent the second data transfer signal. The first data transfer signal causes address detector 31 to start timer 32. However, at this point, both inputs to gate 33 are logic 0. Therefore, if host 10 sends a data transfer instruction to card 11 host 10 will be allowed to access UART 14 exactly as described above. However, if timer 1 has reached a predetermined value then a logic 1 will be placed on conductor 52. This will force the output of gate 33 to a logic 1, which forces the output of gate 27 to be a logic 0, thereby disabling host data buffer 13. Therefore, host 10 is disconnected from bus 40 and UART 14. Furthermore, since host address detector 24 is placing a logic 1 on conductor 44 the output of gate 26 would be a logic 0. This indicates to host 10 that a slow I/O device is being accessed and that the data transfer will take additional time. Host 10 therefore maintains the address and data on bus 12 until the I/O READY signal on conductor 12a is reasserted. Timer 32 therefore allows a host data transfer operation to be performed, even though microprocessor 23 has sent the first data transfer signal, if the host data transfer operation can be completed before microprocessor 23 sends the second data transfer signal. The predetermined value for timer 32 is therefore the difference between the instruction execution time of microprocessor 23 and the data transfer operation time between host 10 and a UART 14 or 15.

Assume now that microprocessor 23 has sent the second signal, which is the actual data transfer operation. Address detector 31 will place a logic 1 on output B, which enables data buffer 30 so that microprocessor 23 can exchange data with UARTs 14 and/or 15. The logic 1 on the B output of address detector 31 also forces the output of gate 33 to a logic 1, thereby forcing the output of gate 27 to a logic 0 which, as described above, isolates host 10 from bus 40. Furthermore, the logic 1 output of gate 33 enables gate 26 so that if host 10 places the UART address on bus 12 host address detector 24 will place a logic 1 on conductor 44 and the output of gate 26 will be a logic 0, thereby deasserting the I/O READY signal. Therefore, data transfer requested by host 10 will be delayed until completion of the data transfer by microprocessor 23. Once microprocessor 23 has completed the data exchange then it will change the signals on processor bus 42 and address detector 31 will place logic 0's on outputs A and B.

It will be appreciated from the above that microprocessor 23 may be considered a superior device, even though it is a slower device, because it is always granted immediate access to the bus 40 when it sends the second signal. Host 10 may be considered to be a subordinate device, even though it is a faster device, because a data transfer operation requested by host 10 may be delayed until completion of a data transfer operation by microprocessor 23.

Turn now to FIG. 2 which is a flow chart of the operation of the interface circuit of the present invention. This operation is performed by controller 25 of interface circuit 22 in FIG. 1. Decision 70 determines whether there is a host access request. If not then any requested microprocessor data transfers are conducted 71. If there is a host access request then decision 72 determines whether a microprocessor data transfer is currently in progress. If so then in step 73 the I/O READY line is deasserted and the microprocessor data transfer is continued. At the completion of the microprocessor data transfer then, in step 74, the I/O READY signal is asserted and the host data transfer operation is conducted. After the host data transfer is completed a return is made to decision 70.

In decision 72, if a microprocessor access not in progress then decision 75 determines whether there is a pending microprocessor access request. If not then step 74, which conducts the host access, is executed. If a microprocessor access request is pending then decision 76 determines whether a timeout condition has occurred. If not then there is still sufficient time for the host to accomplish a data transfer before the microprocessor is ready to begin a data transfer. Therefore, step 74, which performs the host access, is executed. If a timeout condition has occurred then there is insufficient time remaining before the microprocessor data transfer will begin. Therefore, in step 73 the I/O READY line is deasserted and the microprocessor data transfer is conducted. When the microprocessor data transfer is completed then, in step 74, the I/O READY signal is reasserted and the host data transfer is conducted.

It will therefore be seen that a data transfer by the microprocessor, which has no capability for waiting, is executed when requested by the microprocessor. However, a data transfer by the host, which has the capability for waiting, will be delayed if a microprocessor data transfer is in progress or if there is insufficient time remaining before the microprocessor data transfer commences. Therefore, the delay or waiting time experienced by the host is minimized.

From the above it will be appreciated that the present invention describes a method and apparatus for preventing bus contention problems by requiring a first processing device to signal its intent to access the bus prior to performing a data transfer operation, and delaying a data transfer requested by a second processing device if the data transfer could not be completed prior to commencement of the data transfer requested by the first processing device. Although the preferred embodiment of the present invention has been described with particularity, it will be understood that numerous modifications and variations are possible. Accordingly, the scope of the present invention is to be limited only by the claims below.

What is claimed is:

1. In a system having a fast processor and a controller and a peripheral device connected by a bus, said bus being used for data transfer operations, and a slow processor connected to said controller, connecting said slow processor to said bus to allow data transfer operations between said slow processor and said peripheral device, a method of responding to initiation of a data transfer operation by said fast processor, comprising:

a controller procedure comprising the steps of:
if said slow processor is currently using said bus then instructing said fast processor that said data transfer operation initiated by said fast processor is not complete and denying said fast processor access to said bus until said slow processor has finished using said bus;
if said slow processor has sent a notice of intent to access said bus and said notice has been pending for at least a first predetermined period of time then instructing said fast processor that said data transfer operation initiated by said fast processor is not complete and denying said fast processor access to said bus until such slow processor has finished using said bus; and
otherwise, granting said fast processor access to said bus; and a slow processor procedure comprising the steps of;
sending said notice of intent to access said bus, said notice of intent to access comprising sending either a read signal or a write signal to said controller;
waiting a second predetermined period of time; and
performing a data transfer operation using said bus, said data transfer operation comprising sending said read signal or said write signal again.

2. The method of claim 1 wherein each step of instructing comprises:
deasserting an input/output operation ready signal.

3. The method of claim 2 wherein said system further comprises a bidirectional three-state buffer interposed between said fast processor and said bus, and each step of denying said fast processor access to said bus comprises forcing said buffer into an open-circuit mode.

4. The method of claim 1 wherein said initiation of said data transfer operation by said fast processor comprises said fast processor sending a predetermined device address to said controller.

5. The method of claim 1 wherein said second predetermined period is an instruction execution time for said slow processor.

6. The method of claim 1 wherein said first predetermined period is the difference between an instruction execution time for said slow processor and a data transfer operation time for said peripheral device and said fast processor.

7. In a system having a fast processor and a slow processor and a peripheral device connected to a bus, an apparatus interposed between said fast processor, said slow processor, and said bus for preventing bus contention problems by controlling access to said bus, said apparatus comprising:
first means for providing a time signal when an elapsed time has exceeded a predetermined value;
second means responsive to a first signal from said slow processor for starting said first means, and to a second, subsequent signal from said slow processor for connecting said slow processor to said bus;
third means responsive to either said slow processor being connected to said bus or to provision of said time signal, or both, for providing a bus busy signal;
fourth means responsive to provision of said bus busy signal, after a data transfer operation has been initiated by said fast processor and while said data transfer operation is pending, by sending a status signal to said fast processor, said status signal instructing said fast processor that said data transfer operation is not complete; and
fifth means connected between said fast processor and said bus and responsive to provision of said bus busy signal for isolating said fast processor from said bus.

8. The apparatus of claim 7 wherein said fourth means sends said status signal by deasserting an input/output ready signal.

9. The apparatus of claim 7 wherein said fifth means comprises a bidirectional three-state buffer.

10. The apparatus of claim 7 wherein said bus is a bidirectional data bus.

11. The apparatus of claim 7 wherein said slow processor waits a predetermined period of time between sending said first signal and sending said second signal.

12. The apparatus of claim 11 wherein said predetermined period of time is an instruction execution time for said slow processor.

13. The apparatus of claim 7 wherein said predetermined value is the difference between an instruction execution time for said slow processor and a data transfer operation time between said peripheral device and said fast processor.

14. The apparatus of claim 7 wherein said peripheral device comprises a universal asynchronous receiver transmitter.

15. An apparatus for use with a host computer and a communications device, comprising:
   a microprocessor for controlling said apparatus;
   a peripheral device for communicating with said communications device;
   a bus for connecting said peripheral device to said host computer;
   first means for providing a time signal when an elapsed time has exceeded a predetermined value;
   second means responsive to a first signal from said microprocessor for starting said first means, and to a second, subsequent signal from said microprocessor for connecting said microprocessor to said bus;
   third means responsive to either said microprocessor being connected to said bus or to provision of said time signal, or both, for providing a bus busy signal;
   fourth means responsive to provision of said bus busy signal after a data transfer operation has been initiated by said host computer and while said data transfer operation is pending by sending a status signal to said host computer, said status signal instructing said host computer that said data transfer operation is not complete; and
   fifth means connected between said fast processor and said bus and responsive to provision of said bus busy signal for isolating said host computer from said bus.

16. The apparatus of claim 15 wherein said fourth means sends said status signal by deasserting an input/output ready signal.

17. The apparatus of claim 15 wherein said fifth means comprises a bidirectional three-state buffer.

18. The apparatus of claim 15 wherein said bus is a bidirectional data bus.

19. The apparatus of claim 15 wherein said microprocessor waits a predetermined period of time between sending said first signal and sending said second signal.

20. The apparatus of claim 19 wherein said predetermined period of time is an instruction execution time for said microprocessor.

21. The apparatus of claim 15 wherein said predetermined value is the difference between an instruction execution time for said microprocessor and a data transfer operation time between said peripheral device and said host computer.

22. The apparatus of claim 15 wherein said peripheral device comprises a universal asynchronous receiver transmitter.

* * * * *